United States Patent [19]
Sorette

[11] Patent Number: 5,830,764
[45] Date of Patent: *Nov. 3, 1998

[54] METHODS AND REAGENT COMPOSITIONS FOR THE DETERMINATION OF MEMBRANE SURFACE AREA AND SPHERICITY OF ERYTHROCYTES AND RETICULOCYTES FOR THE DIAGNOSIS OF RED BLOOD CELL DISORDERS

[75] Inventor: Martin P. Sorette, Brighton, Mass.

[73] Assignee: Bayer Corporation, Tarrytown, N.Y.

[21] Appl. No.: 745,830

[22] Filed: Nov. 12, 1996

[51] Int. Cl.$^6$ ..................................................... G01N 33/48
[52] U.S. Cl. ............................... 436/63; 436/10; 436/17; 436/18; 436/116; 436/174; 435/2; 435/29; 435/30
[58] Field of Search .................................... 436/8, 10, 17, 436/18, 63, 73, 79, 164, 166, 172, 174; 435/2, 29, 30, 34; 252/408.1

[56] References Cited

U.S. PATENT DOCUMENTS

| | | | |
|---|---|---|---|
| 4,412,004 | 10/1983 | Ornstein et al. | 436/10 |
| 4,575,490 | 3/1986 | Ornstein et al. | 436/63 |
| 4,735,504 | 4/1988 | Tycko | 356/336 |
| 5,284,771 | 2/1994 | Fan et al. | 436/10 |
| 5,350,693 | 9/1994 | Colella et al. | 436/63 |
| 5,411,891 | 5/1995 | Fan et al. | 436/63 |
| 5,633,167 | 5/1997 | Fan et al. | 436/17 |

OTHER PUBLICATIONS

Lew et al. "Generation of normal human red cell volume . . ." *Blood*, vol. 86, No. 1, pp. 334–341, 1995.
Ponder, E. Hemolysis and related phenomenon. Grune & Stratton, New York. 1948 reissued 1971. pp. 10–26.
Evans EA and Fung YC. Improved measurements of the erythrocyte geometry. Microvasc. Res. 4: 335, 1972.
Engstrom KG, Moller B. and Meiselman HJ. Optical evaluation of red blood cell geometry using micropipette aspiration. Blood Cells 18: 241–258, 1992.
Engstrom KG and Meiselman HJ. Optical and mathematical corrections of micropipette measurements of red blood cell geometry during anisotonic perfusion. Cytometry 17: 279–286, 1994.
Nash GB and Wyard SJ. Changes in surface area and volume measured by micropipette aspiration for erthrocytes aging in vivo. Biorheology 17: 479–848, 1980.
Clark MR, Mohandas N, and Shohet SB. Osmotic gradient ektacytometry: comprehensive characterization of red cell volume and surface maintenance. Blood 61: 899–910, 1986.
Bessis M, Mohandas N and feo C. Automated ektacytometry: a new method of measuring red cell deformability and red cell indices. Blood Cells 6: 315–327, 1980.
Rose HG and Oklander M. Improved method for the extraction lipids from human erythrocytes. J. Lipid Res 6: 428–431, 1965.
Reed CP, Swisher SN, Marionetti GV, Eden EG. Studies of the lipids of the erythrocyte I. Quantitative analysis of the lipids of normal human red cells. J Lab. Clin. Med. 56: 281–289, 1960.

Winterbourne CC, Batt RD., Lipid composition of human red cells of different ages. Biochem. Biophys. Acta. 202: 1–8, 1970.
Kim YR and Ornstein L. Isovolumetric sphering of erythrocytes for more accurate and precise cell volume measurement by flow cytometry. cytometry 3: 419–427, 1983.
Tycko DH, Metz MH, Epstein EA and Grinbaum A. Flow Cytometric light scattering measurement of red blood cell volume and hemoglobin concentration. Applied Optics 24: 1355–1365, 1985.
Mohandas N. Kim YR, tycko HD, Orlik J, Wyatt J and Groner W. Accurate and independent measurement of volume and hemoglobin concentration of individual red cells by laser scattering. Blood 68: 506–513, 1986.
Eber SW, Pekrun A, Neufeldt A, and Schroter, W. Prevalence of increased osmotic fragility of erythrocytes in German blood donors: screening using a modified glycerol lysis test. Ann. Hamatol. 65:m 88–92, 1992.
Acharya J, Ferguson IL, Cassidy AG and Grimes AJ. An improved acidified glycerol lysis test (AGLT) used to detect spherocytosis in pregnancy. Br. J. Haematol 65: 343–345, 1987.
Bucx P, Breed WPM and Hoffman JJM. Comparison of acidified glycerol lysis test, pink test and osmotic fragility test in hereditaru spherocytosis: effect of incubation. Eur. J. Haematol 40: 277–231, 1988.
Gottfried EL, and Robertson NA. Glycerol lysis time as a screening test for erythrocyte disorders. J. Lab. Clin. Med. 84: 746–751, 1974.
Parpart AK, Lorenz PB, Parpart ER, Gregg JR and Chase A. The osmotic resistance (fragility) of human red cells. J. Clin. Invest. 26: 636–645, 1974.
Rutherford CJ. Postlewaight BF and Hallowes M. An evaluation of the acidified glycerol lysis test. Br. J. Haematol. 63: 119–121, 1986.
Vettore L, Zanella A. Molero GL, DeMatteis MC, Pavesi M, Mariani M. A new test for the laboratory diagnosis of spherocytosis. Acta Hematol. 72: 258–263, 1984.

(List continued on next page.)

*Primary Examiner*—Maureen M. Wallenhorst
*Attorney, Agent, or Firm*—Morgan & Finnegan, L.L.P.

[57] ABSTRACT

The invention describes improved methods and reagent compositions employed therein to determine the existence of blood disorders such as hemolytic anemias in a blood sample obtained from an individual. The methods are preferably carried out on an automated flow cytometer and encompass determining if the individual's red blood cells have undergone a loss of membrane surface area by providing measurements of the surface area and the sphericity of the red blood cells in a whole blood sample as a function of osmolality. The method and reagent compositions used therein provide for the first time accurate measurements of the surface areas of both the mature red blood cell and the reticulocyte populations in a whole blood sample. The method and reagents of the invention promise to shed new insights into reticulocyte membrane remodeling in various red cell disorders.

88 Claims, 2 Drawing Sheets

OTHER PUBLICATIONS

Zanella A, Izzo C, Rebulla P, Zanuso F, Perroni L, and Sirchia G. Acidified glycerol lysis test: a screening test for spherocytosis. Br. J. Haematol. 45: 481–486, 1980.

Godal HC and Heisto H. High prevalence of increase osmotic fragility of red blood cells among Norwegian blood donors. Scand. J. Haematol. 27: 30–34, 1981.

Godal HC, Nyvold N and Rustad A. The osmotic fragility of red blood cells: a re–evaluation of technical conditions. Scand. J. Haematol 23: 55–58, 1979.

Godal HC Elde AT, Nyvold N and Brosstad F. The normal range of osmotic fragility of red blood cells. Scand. J. Haematol. 25: 107–112, 1980.

Fugawa N, Friedman S, Gill FM, Schwartz E and Shaller C. Hereditary spherocytosis with normal osmotic fragility after incubation. JAMA 242: 63–64, 1979.

Cynober T, Mohandas N and Tchernia G. Red cell abnormalities in hereditary spherocytosis–relevance to diagnosis and for understanding the variable depression of clinical severity. J.Lab. Clin. Med., 128: 259–269, 1996.

FIG. 1A

MCV as a function of osmolarity

FIG. 1B

RBC count as a function of osmolarity

FIG. 2

METHODS AND REAGENT COMPOSITIONS FOR THE DETERMINATION OF MEMBRANE SURFACE AREA AND SPHERICITY OF ERYTHROCYTES AND RETICULOCYTES FOR THE DIAGNOSIS OF RED BLOOD CELL DISORDERS

FIELD OF THE INVENTION

The invention relates to methods and reagent compositions which provide a measure of the surface area and sphericity of red blood cells (erythrocytes). Loss of membrane surface area and the consequent increase in sphericity is a characteristic feature of red blood cell disorders such as hereditary spherocytosis, hereditary elliptocytosis and pyropoikelocytosis. The invention promises to improve the detection and determination of blood disorders and to aid in the diagnosis of these hemolytic anemias.

BACKGROUND OF THE INVENTION

Measurements of both red blood cell surface area and surface area to volume ratio (i.e., osmotic fragility) have been used to characterize human erythrocytes and as aids in the diagnosis of red blood cell membrane disorders. Ponder (Ponder, E., Hemolysis and related phenomena. Grune & Stratton, New York, 1948, reissued 1971, pp. 1026) reviewed a number of microscopic approaches to yield a determination of red cell volume and calculation of surface area. These approaches included photography of individual red cells standing on edge, so that from a geometric standpoint the red cell is a solid of revolution about an axis joining the central points of its two biconcavities. To calculate the surface area, a cross sectional outline of the red cell is drawn and the surface area is determined using Pappus' Theorem for the surface of a solid of revolution about an axis, Area=4 $\pi$1 x, where "1" is the length of a quadrant of arc in cross sectional view and "x" is the coordinate of its center of gravity.

Evans and Fung (Evans E. A. and Fung Y. C., Improved measurements of the erythrocyte geometry, *Microvasc. Res.*, 4:335, 1972) developed a quantitative optical processing technique, called micropipette aspiration, which significantly improved accuracy in measuring surface area and volumes of red blood cells. A maximal surface area can be calculated following osmotic manipulation of the surrounding medium (Engstrom K. G. et al., Optical evaluation of red blood cell geometry using micropipette aspiration, *Blood Cells,* 18:241–258, 1992; Engstrom K. G. and Meiselman H. J., Optical and mathematical corrections of micropipette measurements of red blood cell geometry during anisotonic perfusion. *Cytometry,* 17:279–286, 1994). Volume and surface area changes in erythrocytes aging in vivo have been documented using this technique (Nash G. B. and Wyard S. J., Changes in surface area and volume measured by micropipette aspiration for erythrocytes aging in vivo. *Biorheology,* 17:479–484, 1980).

Osmotic gradient ektacytometry, using a specialized laser couette viscometer, quantifies cellular deformability as a function of the tonicity of the suspending medium. Red blood cell deformability is regulated by surface area, surface area to volume ratio, and the state of cell hydration. The maximum value of deformability index attained at physiologically relevant osmolality ("$Di_{max}$") in the absence of changes in membrane rigidity is quantitatively related to the mean surface area of the red cells (Clark M. R. et al., Osmotic gradient ektacytometry: comprehensive characterization of red cell volume and surface maintenance. *Blood,* 61:899–910, 1983; Bessis M. et al., Automated ektacytometry: a new method of measuring red cell deformability and red cell indices. *Blood Cells,* 6:315–327, 1980). Unlike the present invention, the osmotic gradient ektacytometry method, in addition to other manual measurement methods, require specialized equipment and an usual degree of technical skill to obtain accurate measurements. Moreover, such methods cannot distinguish mature from immature red blood cells in a whole blood sample.

The erythrocyte membrane is composed of a lipid bilayer and membrane proteins. The lipid bilayer contains phospholipids and cholesterol as the major constituents which are present in almost equimolar amounts. A physicochemical approach for estimating membrane surface area is the measurement of membrane lipid content as described in Rose H. G. and Oklander M., Improved method for the extraction of lipids from human erythrocytes, *J. Lipid Res.,* 6:428–431, 1965; Reed C. P. et al., Studies of the lipids of the erythrocyte I. Quantitative analysis of the lipids of normal human red cells, *J. Lab. Clin. Med.,* 56:281, 1960; Winterbourne C. C. and Batt R. D., Lipid composition of human red cells of different ages. *Biochem. Biophys. Acta.,* 202:1–8, 1970).

A method for isovolumetric red cell sphering, staining of reticulocytes, and determination of red blood cell and reticulocyte indices by flow cytometry have been described in U.S. Pat. Nos. 4,575,490 and 4,412,004 to Kim and Ornstein and in a publication by Kim Y. R. and Ornstein L. (Isovolumetric sphering of erythrocytes for more accurate and precise cell volume measurement by flow cytometry, *Cytometry,* 3:419, 1983). Kim and Ornstein (1983, *Cytometry,* 3:419) teach a method for the elimination of orientational noise in the measurement of the volume of red blood cells in a flow cytometer. Their method involves isovolumetric sphering of unstained red blood cells to eliminate orientational differences between the cells to permit more precise and accurate measurement of cell volume. Each red blood cell is converted from a biconcave shape to a perfect sphere by anionic surfactant as a sphering agent, including fixative or protein buffering to prevent cell lysis by the surfactant.

U.S. Pat. No. 4,735,504 to Tycko and a paper by Tycko et al., (Flow cytometric light scattering measurement of red blood cell volume and hemoglobin concentration, *Applied Optics,* 24:1355–1365, 1985), describe the red blood cell channel of the BAYER-TECHNICON H●1™system, a commercially available flow cytometer which provides a fully automated method and means for determining the individual and mean erythrocyte volumes, and individual and mean corpuscular hemoglobin concentrations of erythrocytes. In this method, red blood cells are diluted and then isovolumetrically sphered using the Kim and Ornstein method. After a twenty second incubation period, the cells are passed, essentially one at a time, through the illuminated measurement zone within the red cell channel of the analyzer. The magnitude of the light scattered by these cells into two angular intervals is measured. When the light source is a helium neon laser which emits light at 633 nm, the two scattered light collection intervals are two to three degrees and five to fifteen degrees. Once the level of scattered light in each interval is known for a given cell, the volume and hemoglobin concentration for that cell are determined by comparison with values predicted by Mie scattering theory. This method has been demonstrated to give accurate volume and hemoglobin concentration measurements compared with reference methods (Mohandas N. et al., Accurate and independent measurement of volume and hemoglobin concentration of individual red cells by laser light scattering, *Blood*, 68:506–513, 1986 ).

U.S. Pat. Nos. 5,438,003 and 5,350,695 to Colella et al. describe reagent compositions and methods for use in the identification and characterization of reticulocytes in whole blood for use in absorption/scatter flow cytometry. A zwitterionic detergent is used to isovolumetrically sphere cells in the presence of organic cationic dyes for staining reticulocytes in a blood sample. The volume and hemoglobin concentration of reticulocytes can be determined independently from mature erythrocytes.

In spite of the several prior art approaches enumerated above for obtaining cell surface area measurements, a number of real problems exist in the use of these approaches by the skilled practitioner. Specifically, the above-described photomicrographic graphic techniques are tedious because the cells must be photographed individually, and many cells have to be photographed to randomly find and distinguish a cell which is standing exactly on its edge in sharp focus. Accuracy of the measurement is also questionable because of the uncertainty of the relation of the cell edge to the diffraction bands which replace it in the image. In addition, although the micropipet method provides accurate surface area measurements on individual red blood cells, the method is extremely time consuming, labor-intensive and requires a high level of technical skill using specialized equipment, thus limiting its application for routine clinical use. Another disadvantage of the micropipet method is that it is not suitable for routine quantification of the cellular parameters of surface area, volume and sphericity for large populations of red cells. Furthermore, despite the fact that osmotic gradient ektacytometry and biochemical measurement of membrane lipids provide quantitative correlates to the mean cell surface area, these techniques also have limited applicability and efficiency for routine clinical use.

Unlike the labor-intensive and clinically inapplicable prior art methods, the present invention provides a rapid, convenient and clinically relevant method for accurately determining the surface area and sphericity of red blood cells and reticulocytes by using a novel series of reagents combined with flow cytometric analysis using a conventional hematology analyzer (e.g., the BAYER-TECHNICON H●3™). The invention is especially suitable for semi-automated and automated hematology analyzers. The method of the invention is distinguished from and is an improvement over all former techniques in that the invention can provide an accurate and reliable measurement of the surface area of the youngest red blood cells (reticulocytes) independently from that of the mature red blood cell population.

SUMMARY OF THE INVENTION

Accordingly, it is an object of the present invention to provide an improved method and reagent composition for providing a measurement of the surface area and the sphericity of red blood cells for diagnosing hemolytic anemias, such as hereditary spherocytosis, hereditary elliptocytosis, and pyropoikelocytosis by absorption/scatter and fluorescence flow cytometry. In accordance with the invention, a novel series of reagents having different osmolalities combined with flow cytometry analysis are used to achieve the rapid and convenient methods as described, particularly for semi-automated and fully-automated flow cytometry analysis.

Another object of the present invention is to provide methods and reagent compositions employed therein for measuring the surface area of the immature red blood cell population (reticulocytes) independently from measuring the erythrocyte population in a whole blood sample using hematology analyzers.

A further object of the present invention as described above is to provide a means to determine the maximal cell surface area rather than a surface to volume ratio, thereby allowing for the diagnosis and/or determination of larger numbers of difficult-to-detect cases of blood cell disorders, particularly, hereditary spherocytosis.

Yet another object of the present invention is to provide methods and reagent compositions for identifying for blood banking purposes those units of blood which will have decreased survival over time due to the loss of cell surface area.

Still yet another object of the present invention is to provide methods and reagent compositions for differentially determining the surface area of reticulocytes as distinguished from mature red blood cells by including a cationic dye to stain the RNA of reticulocytes in the reagent compositions and analyzing the cells by flow cytometry.

Yet another object of the invention is to use the methods and reagent compositions in accordance with the invention in quality assurance of donor blood samples for blood banking, i.e., in the identification of those units of blood which would have decreased survival time upon storage, due to storage lesion, for example.

Further objects and advantages afforded by the invention will be apparent from the detailed description hereinbelow.

DESCRIPTION OF THE DRAWINGS

The above and other objects and significant advantages of the present invention are believed to be made clear by the following detailed description thereof taken in conjunction with the accompanying drawings wherein:

FIG. 1A shows that cell volume increases with decreasing osmolality until a critical hemolytic volume is reached. FIG. 1B shows that the critical maximum volume (as determined in FIG. 1A) are determined at the point where 50% of the cells have lysed, by examining the intersecting lines in the graph of RBC Count (% of control; y axis) as a function of osmolality (x axis).

DETAILED DESCRIPTION OF THE INVENTION

The invention provides an improvement in methods used to diagnose blood cell disorders, particularly red blood cell membrane disorders such as hereditary spherocytosis (HS), which is one of the most common congenital hemolytic anemias, having an overall estimated incidence in northern Europe and the United States of about 200 to 300 cases per million. The methods and reagent compositions employed therein are particularly suitable for use in both semi-automated and fully-automated hematology analyzers using absorption/scatter flow cytometry. A number of hematology analysis systems can be employed to practice the methods and compositions of the invention and are available to the skilled practitioner in the art; among them are the BAYER-TECHNICON H●1™, H●2™ and H●3™ series of analyzers which are commercially available from the assignee hereof. The BAYER-TECHNICON H●3™ instrument is particularly capable of providing an independent measurement of reticulocyte indices (i.e., volume), thereby allowing the measurement of reticulocyte surface area in accordance with the invention. However, any analyzer having the capability of accurately measuring the volume of sphered red blood cells could be used to determine the surface area of a reticulocyte population using the reagents described herein, including the general class of electrical impedance instruments used to perform aperture impedance technology, such as those manufactured by Coulter. However, the Coulter analyzers do not discriminate between reticulocyte and red blood cell indices. Further, the volume measurement obtained by aperture impedance is affected by cell shape, thereby resulting in a need for different calibration for biconcave versus sphered red blood cells, which does not allow the method to be performed in the usual instrument mode for clinical analysis. Those having skill in the art will further appreciate that manual microscopic analysis methods can also be used with the reagent compositions as described herein.

The method of the invention provides diagnostic specificity of red blood cell membrane disorders because the invention achieves the measurement of maximal cell surface area, and not merely a surface to volume ratio. Importantly, the invention allows the discrimination of mature red blood cells from the immature reticulocyte population and the direct determination of surface area (and thus the concomitant loss thereof) of both cell populations. In current practice, osmotic fragility tests and various glycerol lysis tests are used to screen for HS, but such tests have been shown to overlook the diagnosis of a subset of cases that have recently been estimated as afflicting more than 30% of individuals having the disease. These overlooked cases occur because the cells appear to have a normal, rather than an aberrant, osmotic fragility value. Using the available methods, an osmotic fragility value in the normal range can be erroneously determined in these HS cases, due to the decrease in both surface area and cell volume of the diseased cells, which yields a pseudo "normal" surface area to volume ratio, thus resulting in an osmotic fragility in the normal range.

The method of the present invention is carried out as generally described hereinbelow for use with an automated or semi-automated analyzer. An aliquot of a sample of blood is added at a known dilution to a series of aqueous reagent compositions (also called reagents or reagent solutions herein) which comprise a buffer, e.g., phosphate buffer or a buffering salt such as Tris, Tris HCl, and the like (Table 1); a surfactant, i.e., a zwitterionic, nonionic, or cationic surfactant, as sphering agent for red blood cells and reticulocytes (Table 2); and a salt, i.e., a metal salt, such as sodium chloride, potassium chloride, lithium chloride, at concentrations sufficient to provide solutions with defined osmolalities which are in the range of about 290 milliosmoles to about 50 milliosmoles (mOsm). When a cationic dye is used to stain reticulocytes, the zwitterionic, nonionic, or cationic surfactant should be compatible with such cationic dye. The surfactants presented in Table 2 are compatible with cationic reticulocyte staining dyes such as Oxazine 750. The pH range for the reagent solutions is, in general, near physiological, i.e., from about 6 to about 9, preferably about 7 to 8, more particularly, 7.4 to 7.6.

TABLE 1

| Buffering Salt | Concentration (mM) |
|---|---|
| Tris/Tris HCl (Tris[hydroxymethyl]amino-methane) | 5–20 |
| MOPS (3-[N-Morphilino]-propanesulfonic acid) | 5–20 |
| HEPES (n-[2-Hydroxyethyl]-piperazine N' [2 ethanesulfonic acid]) | 5–20 |
| DIPSO (3-[N,N-bis(2-hydroxyethyl)-amino-]-2 hydroxypropane sulfonic acid) | 5–20 |
| Na or K phosphate | 5–20 |

TABLE 2

| Surfactant | Concentration |
|---|---|
| TDAPS (N-tetradecyl-N,N-dimethyl-3-ammonio-1 propanesulfonate) | 3.9–11.8 µg/ml |
| DDAPS (N-dodecyl-N,N-dimethyl-3-ammonio-1 propanesulfonate) | 49.3–148 µg/ml |
| Lauramidopropylbetaine | 12–87.5 µg/ml |
| Cocoamidopropylbetaine | 8.8–17.5 µg/ml |
| Cocoamidosulfobetaine | 12.5–15.0 µg/ml |
| Nonidet P-40 (NP-40) | 0.005%–0.01% |
| Triton X-100 | 0.005%–0.01% |

Depending upon the hematology analyzer instrument employed, blood sample aliquot size is governed by three factors: the total volume needed for the instrument to make the measurement, including the "dead space" volume which is aspirated by the instrument but not analyzed, the concentrations of surfactant and dye, if used, relative to the concentration of cells, and the ability of the instrument to discriminate individual cells. For the BAYER-TECHNICON H●™ series of instruments, using the concentrations of dye and surfactant described in the examples, the blood sample size can be in the range of about 1 µl to 120 µl, depending upon the mode of dilution. For example, a blood sample aliquot as small as 1 µl could be used if the dilution is made manually, while an aliquot of up to about 120 µl if the blood sample is aspirated in a fully automated mode, e.g., with approximately 2 µl diluted for the measurement, approximately 118 µl of blood fills the hydraulic pathway or "dead space"). The preferred dilution ratio of whole blood to reagent composition is about 1:625 to 1:1000 for the BAYER-TECHNICON H●™ series of instruments.

In general, the aqueous reagent compositions employed in the method of the invention comprise discrete compositions which are identical except that they have different osmolalities provided by different effective concentrations of metal salt in each of the compositions. The reagent solution series used in the method of the invention provide the ability to determine at least two parameters that are critical for the method, namely, the volume and surface area at isotonicity (i.e., physiologic osmotic pressure), and the volume and surface area at the critical hemolytic volume, i.e., the point at which 50% of the cells have lysed. There is a range for the critical hemolytic volume. Depending upon the nature of the blood sample, the potential range for this point spans an osmotic range having values from about 290 mOsm to about 50 mOsm, and more particularly, about 260 to about 100 mOsm. Thus, a series of reagent compositions can be prepared having osmolalities from about 290 mOsm to 50 mOsm, or more particularly about 260 to about 100 mOsm, wherein the series can contain at least four compositions.

For most samples, the osmotic range from the onset of cell lysis until complete cell lysis is a narrow one. Thus, more, e.g., from about 4 to 20, preferably 15 or 16, reagent compositions with progressively "finer" increments in osmolality, as described and used in the series, will increase the overall accuracy. Fewer reagent compositions which span a finite osmotic range can also be used to provide coarse increments in osmolality; however, those in the art will appreciate that coarse increments, although useful, may decrease the overall sensitivity and/or accuracy of the assay. For performing the method of the invention, reagent compositions, i.e., reagent solutions, having particular osmolalities are necessary to determine at least one point at isotonicity (i.e., physiologic osmotic pressure) and at least three points to be confident that the critical hemolytic volume has been reliably determined with accuracy. More specifically, for use in the method, one reagent composition is prepared having an osmolality of approximately 290 mOsm (i.e., physiologic osmotic pressure) and at least three compositions are prepared having different osmolalities that fall within the hemolytic curve for the (test) sample under study as described above.

For the testing of blood samples at random, a fairly broad range of osmolalities (e.g., approximately 290 to 50 mOsm, or 260 to 100 mOsm) are necessary to perform the method, due to true biological variation and the different testing conditions in which the method may be used. For normal blood samples (e.g., normal freshly-drawn bloods), this would span a range of about 100 to 180 mOsm (±about 1 to 10 mOsm, preferably, about ±3 to 6 mOsm), and preferably a range of about 120 to 160 mOsm (±about 1 to 10 mOsm, preferably about ±3 to 6 mOsm).

As a more particular, but nonlimiting, example of a reagent series representing finer increments in osmolality to achieve more accurate results using the method in accordance with the invention, the final or target osmolalities of the compositions may be as follows: a series of reagents having 15 different osmolalities of 290, 270, 240, 210, 200, 180, 170, 160, 150, 140, 130, 120, 110, 80 and 50 mOsm. Final osmolalities suitable for use in the invention are at about ±1 to 10 mOsm, preferably, about ±2 to 8 mOsm, more preferably, about ±3 to 6 mOsm of the target value and are confirmed by freezing point.

The reagent series may also include a cationic dye compound (e.g., the oxazines, such as Oxazine 750 and Brilliant Cresyl Blue or the thiazines, such as New Methylene Blue) to stain the RNA of the reticulocytes in the sample in order to distinguish the reticulocytes from the mature red blood cells by absorption at 633 nm in the absorption channel of the instrument. For semi-automated analysis, the dye compound Oxazine 750, for example, is present in the reagent compositions at a concentration of about 1 $\mu$g/ml to about 25 $\mu$g/ml, preferably about 2 $\mu$g/ml to about 15 $\mu$g/ml, and the blood sample is incubated for about 10 to 90 minutes, preferably about 30 minutes. For fully automated analysis, the dye compound is present in a concentration range of about 6 $\mu$g/ml to about 25 $\mu$g/ml, preferably about 7.6 $\mu$g/ml to about 15 $\mu$g/ml. In addition, using automated analysis instruments, the analyzer automatically mixes the blood sample and the reagent compositions and the mixtures are reacted for about 20 to 60 seconds, preferably about 42 seconds prior to the analytical determinations. In addition, a number of fluorescent dyes, e.g., acridine orange and derivatives thereof, such as described in U.S. Pat. No. 5,411,891 to Fan et al., can be used in conjunction with the appropriate excitation and detection parameters.

Examples of zwitterionic surfactants suitable for use in the reagents and methods of the invention include, but are not limited to, lauramidopropylbetaine, N-tetradecyl-N,N-dimethyl-3-ammonio-1-propanesulfonate (TDAPS),N-dodecyl-N,N-dimethyl-3-ammonio-1-propanesulfonate (DDAPS), cocoamidopropylbetaine and cocoamidosulfobetaine. The concentration of zwitterionic surfactants compatible with the dye compounds and suitable for use in the invention are presented in Table 2. The blood sample may be a whole blood sample, preferably anticoagulated.

After aliquots of the blood sample are incubated in the series of tonicity reagents for a period of time, the cells are analyzed in the red cell/absorption channel of a hematology flow cytometric analyzer, such as the BAYER-TECHNICON H●1™, H●2™ and H●3™ series of analyzers commercially available from the assignee hereof. Cells are enumerated and their volumes are determined according to Mie scatter theory. Using the measurement for cell volume, the individual cell surface area is calculated for cells that are analyzed in each reagent having its specified osmolality and comprising the reagent series. Because the zwitterionic surfactant is capable of sphering cells at all osmotic pressures, the surface area (SA) is derived from the mean cell volume (MCV) as follows below:

$$SA = 4\pi r^2 \qquad (1)$$

$$= 12.57 \, (0.239 \, *MCV)^{2/3} \qquad (2)$$

Sphericity is given by:

$$\frac{4\pi}{(4/3\pi)^{2/3}} \quad \frac{MCV^{2/3}}{SA} \qquad (3)$$

A graphical representation of the osmotic fragility (i.e., the loss of cell number) and the surface area and sphericity as a function of osmolality can then be plotted, as is routinely performed by the practitioner skilled in the art of plotting and interpreting osmotic fragility curves.

The maximal prelytic surface area, the surface area at 50% hemolysis and the sphericity are the values of diagnostic interest that can be ascertained by the use of the invention. Sphericity=1 for a sphere; a value of less than 1 (<1) reflects excess surface area. The maximal prelytic surface area is ascertained by obtaining the mean cell volume (MCV) at the last osmotic point before cell lysis (i.e., decrease in cell count) occurs. This MCV is applied in Equation 2 above. Surface area at 50% hemolysis is derived by Equation 2 using the MCV obtained at the osmotic point where 50% of the cells have lysed, i.e., undergone hemolysis. The 50% hemolysis point is the reportable value for the standard osmotic fragility test. Sphericity calculated by Equation 3 above using $MCV^{2/3}$ determined at maximum MCV and SA determined from maximum MCV provides values about 1.0, which is a predicted value for perfect spheres. This confirms that the geometric assumption of the method, i.e., that the surfactant-treated cells are spheres, is correct. As a particular but nonlimiting example, if $MCV^{2/3}$ determined at 290 mOsm and SA determined at critical hemolytic volume in Equation 3 are applied, sphericity values for the normal blood samples as shown in Example 1, Table 3, range from 0.7019 to 0.7482, with a mean value of 0.7157. The value of less than 1.0 shows that these normal bloods had excess surface area to accommodate the increase in cell volume due to hypotonic swelling.

The morphological microspherocytic cell shape of erythrocytes in hereditary spherocytosis is a result of lipid and transmembrane protein loss from the red cell membrane, i.e., loss of cell surface area. If $MCV^{2/3}$ determined at 290 mOsm and SA determined at critical hemolytic volume in Equation 3 are applied, sphericity values for cells which have lost surface area and become spherocytic will approach a value of 1.0. Thus, any value between the normal value of approximately 0.71 and the value of 1.0 for a perfect sphere indicates the degree of membrane loss that has occurred.

As a practical aspect of the invention, the method and reagents employed therein are used in quality assurance of donor blood samples for blood banking. Red blood cells develop an adverse condition called "storage lesion" when preserved in vitro, one feature of which is the loss of cell surface area. More particularly in this regard, red blood cells during storage shed exocytic microvesicles which contain lipids, band 3 protein, glycophorins and actin. This process, along with changes in other physiological parameters such as decreases in pH, 2,3-DPG and ATP, are termed the "storage lesion in transfusion medicine. Cells suffering from storage lesion have decreased survival in vivo and are therefore less effective in transfusion therapy than are normal cells which function for a longer period of time. By utilizing the method of the invention to obtain maximal surface area and sphericity values at the time of blood donation and at the time of use of units of blood, a rapid quantitative measure can be made for surface area loss (i.e., maximal surface area is decreased and the sphericity value increases from about 0.71 approaching a value of about 1.0). This analysis would have the most practical application in the development of improved stored blood additives and storage containers. Thus, the method of the invention can identify those units of blood which would have decreased storage survival time. Another application of this analysis is in the evaluation of units of blood before transfusion to insure that excessive loss of surface area had not occurred during the approved storage period. Accordingly, the use of red blood cells that may have accelerated clearance from the circulation would be prevented. For plasma transfusion, elimination of units of blood that had demonstrated excessive loss of surface area may reduce the risk of alloimmunization of patients receiving vesicle-containing plasma, since the presence of ABO and Rh blood group epitopes and the M, N, S, s, $Fy^2$ and K blood group antigens on vesicle membranes has been reported.

EXAMPLES

The following examples as set forth herein are meant to exemplify the various aspects of carrying out the invention and are not intended to limit the invention in any way.

Example 1

A series of aqueous reagent compositions for use in the method of the invention were prepared having the range of osmolalities described in accordance with the invention in order to carry out the methods for determining red blood cell and reticulocyte membrane sphericity and fragility. The reagent series was formulated wherein the reagent solutions comprising the series had osmolalities ranging from 50 to 290 mOsm.

Each reagent solution in the series had a base composition comprising sodium phosphate buffer, comprising $Na_2HPO_4$ (1.365g/l) and $NaH_2PO_4$(0.243g/l),pH 7.4, and the zwitterionic detergent N-tetradecyl-N,N-dimethyl-3-ammonio-1-propane sulfonate (TDAPS) at a concentration of 8.0 mg/l. Sodium chloride was added to obtain 15 reagent compositions, each having a different osmolality, with the osmolality range of the series of reagents being within the desired osmolality range, which was confirmed by freezing point to be about ±3 to 6 mOsm of the target value: i.e., 290, 270, 240, 210, 200, 180, 170, 160, 150, 140, 130, 120, 110, 80, 50 mOsm. "about ±3 to 6 mOsm" represents the practical reproducibility specification of the osmolality measurement of each of the reagents using the currently-available commercial freezing point or vapor pressure osmometers. With or without specialized equipment for determining the accuracy of osmolality measurements, the value range of about ±1 to 10 mOsm, preferably about ±2 to 8 mOsm, more preferably about ±3 to 6 mOsm serve as upper and lower limits for the various osmolality determinations for use in the invention. It will be understood by those in the art that any determination of osmolality having an accuracy limit exceeding the described upper limits, e.g., about ±8 to 10 mOsm, might have an adverse impact on the accuracy in the critical range of the reagent composition series in which there were 10 mOsm increments.

Aliquots of freshly drawn blood (i.e., those that had been stored for <8 hours at room temperature) were placed in test tubes, each containing one of the solutions listed above at a final dilution of 1:625, i.e., the ratio of blood to reagent solution (1 µl blood to 624 µl reagent solution), made manually. For the use in semi-automated and automated analyzers, e.g., the BAYER-TECHNICON H●™series of instruments, a dilution in the range of about 1:500 to about 1:1000, preferably, 1:625, can be used with the reagent series. The dilution can be accomplished in an automated mode, for example, using the sample shear valve to deliver a measured volume of blood to a reaction chamber filled with reagent composition solution by syringe or other pump mechanism. After a 30 minute incubation at room temperature, the tubes were mixed three times by inversion and the samples were aspirated though the direct cytometry port of a BAYER-TECHNICON H●3™ automated instrument system. The volume and cell count values are displayed by the computer on the instrument and the instructions regarding instrument operation are available in a users' manual provided with the instrument. In addition, clinical evaluations of the overall performance of this instrument are published in the scientific literature.

Figure 1A:
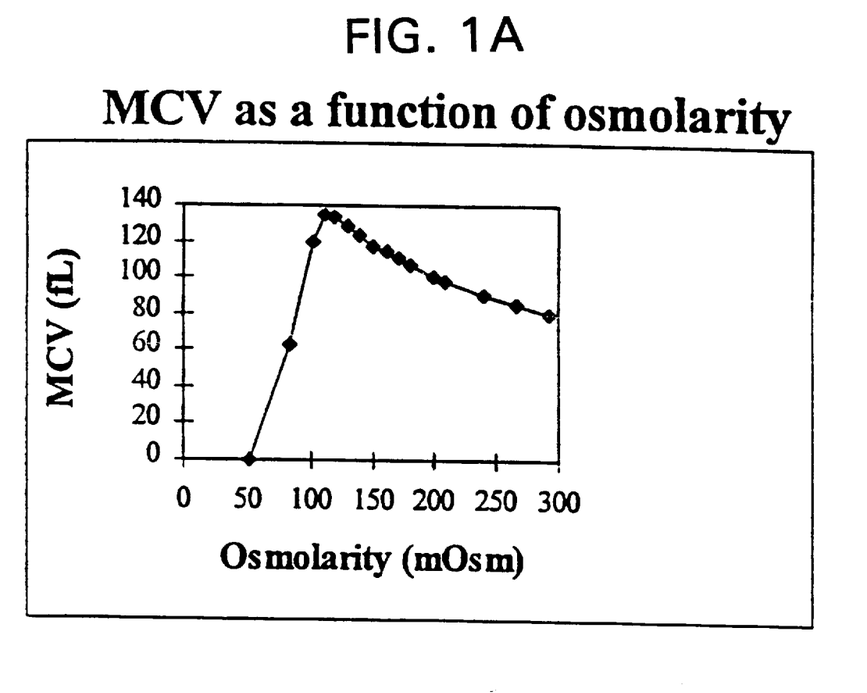
FIGS. 1A and 1B represent the changes in cell volume and cell count as a function of osmolality using fresh blood samples.
Figure 1B:
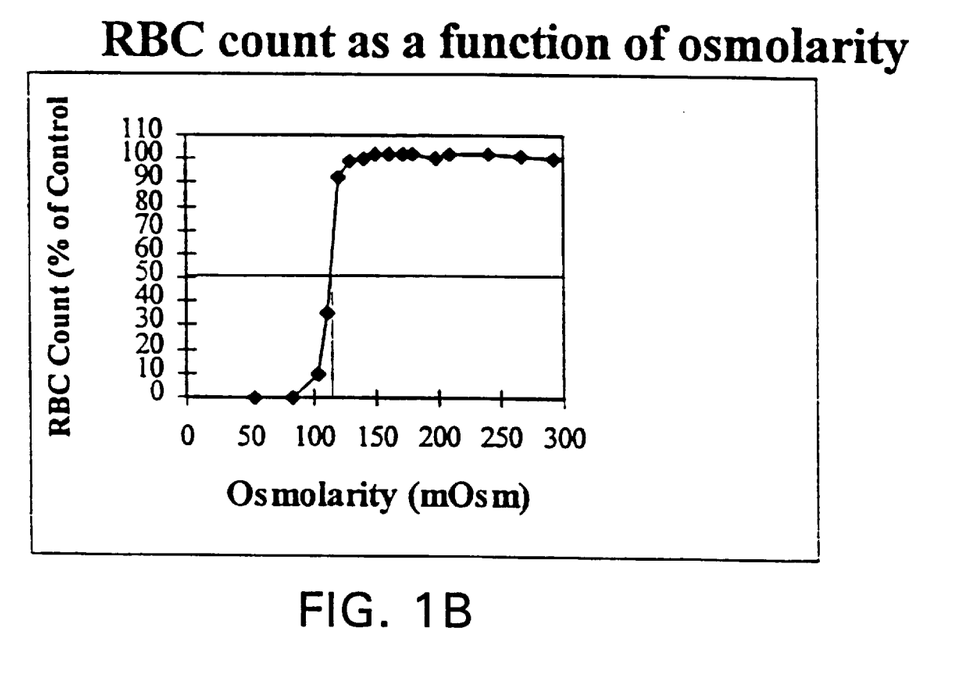

Values for the mean cell volume and the RBC count were obtained from the reticulocyte channel (cross calibrated to the RBC channel). The changes in cell volume and cell count as a function of osmolality are shown in FIG. 1A and FIG. 1B. As can be observed, the cell volume increased with decreasing osmolality until a critical hemolytic volume was reached (FIG. 1A). At the point where 50% of the cells had lysed (as represented at the intersecting lines in FIG. 1B), this critical maximum volume was determined. After obtaining the initial (isotonic) volume and the critical maximum volume, the surface area was derived from the MCV as shown in Equations 1 and 2. Sphericity was then calculated using the $MCV^{2/3}$ from the critical maximum volume and the surface area determined at isotonicity (i.e., approximately 290 mOsm). As an exemplary guide, the following calculations as achieved by the invention are provided: The measured mean cell volume (MCV) at 290 mOsm is 90 fL and the critical hemolytic volume is determined to be 150 fL.

Surface area at 290 mOsm is given by:
12.57 $(0.239 \times 90)^{2/3}$=12.57 (7.718)=97.02.
Maximal surface area is given by:
12.57 $(0.239 \times 150)^{2/3}$=12.57 (10.846)=136.34.
Sphericity is then given by:

$$\frac{4\pi}{(4/3\pi)^{2/3}} \quad \frac{MCV^{2/3}}{SA} \text{ (determined at 290 } mOsm\text{)}$$
$$\text{(determined at critical } V, \text{ or } V\text{max)}$$

= 4.836    $\frac{20.07}{136.34}$

= 4.836    .1472

= Sphericity = 0.711

The results of the analysis of blood samples from ten normal individuals with no known blood abnormalities are shown in Table 3. The volume at physiologic osmotic pressure (290 mOsm)/maximal volume (Vmax) ratio range of 1.62 to 1.70 is consistent with the literature value of 1.67 obtained by Ponder. The average calculated surface area for these samples, 131.5 M², was approximately 6% less than the expected value of 139.6 obtained by micropipette measurements. Those skilled in the art will be aware that there is not a high degree of significance to such a measured difference on the order of 6%. The BAYER-TECHNICON H●3 ™ instrument, when calibrated and controlled according to manufacturer' s instructions, has a ±5.3% variation around the target value for volume of control material. For example, a target volume of 90 fL could have a measured volume of about 85.2 to 94.7, with a calculated surface area of ±4.1% from the nominal value. As would be expected for normal cells with no excess surface area, the sphericity values approached the theoretical value of 1.0 for perfect spheres.

of erythrocytes and are identifiable for the first one to two days after being released from the bone marrow. Along with increased RNA content, reticulocytes normally have a larger membrane surface area which decreases as the reticulocyte matures. In this example and as presented in Table 4, the reticulocyte population has a 12% greater surface area than that of the gated cell population.

In hemolytic anemias such as hereditary spherocytosis, a reticulocytosis of about 5 to 20% is regularly observed. A pathophysiological manifestation of the disease is the loss of membrane surface area over time as the erythrocyte circulates, until it is prematurely removed. By being able to discriminate the newly-released erythrocytes from those that have been circulating in the periphery, a more sensitive measure of membrane surface loss can be determined, since it is not obscured by "averaging" with the reticulocyte population.

TABLE 3

| SAMPLE ID | MCV (fL) at 290 mOsm | MCV max (fL) | V 290 mOsm/ V max | Sphericity (V max/ SA Max) | Sphericity V290 mOsm/SA Max | Surface Area µM² |
|---|---|---|---|---|---|---|
| 1 | 89.1 | 150.6 | 1.69 | 0.9992 | 0.7054 | 136.7 |
| 2 | 91.0 | 147.4 | 1.62 | 1.0317 | 0.7482 | 130.7 |
| 3 | 87.2 | 142.2 | 1.63 | 0.9992 | 0.7217 | 131.7 |
| 4 | 89.6 | 146.3 | 1.63 | 0.9992 | 0.7217 | 134.7 |
| 5 | 74.9 | 126.5 | 1.69 | 0.9993 | 0.7057 | 121.7 |
| 6 | 80.0 | 135.5 | 1.69 | 0.9994 | 0.7044 | 127.4 |
| 7 | 90.1 | 148.4 | 1.65 | 0.9990 | 0.7175 | 135.4 |
| 8 | 76.7 | 130.6 | 1.70 | 0.9995 | 0.7020 | 124.3 |
| 9 | 93.8 | 153.4 | 1.63 | 0.9992 | 0.7210 | 138.4 |
| 10 | 87.9 | 147.2 | 1.67 | 0.9995 | 0.7099 | 134.6 |

Example 2

Figure 2:
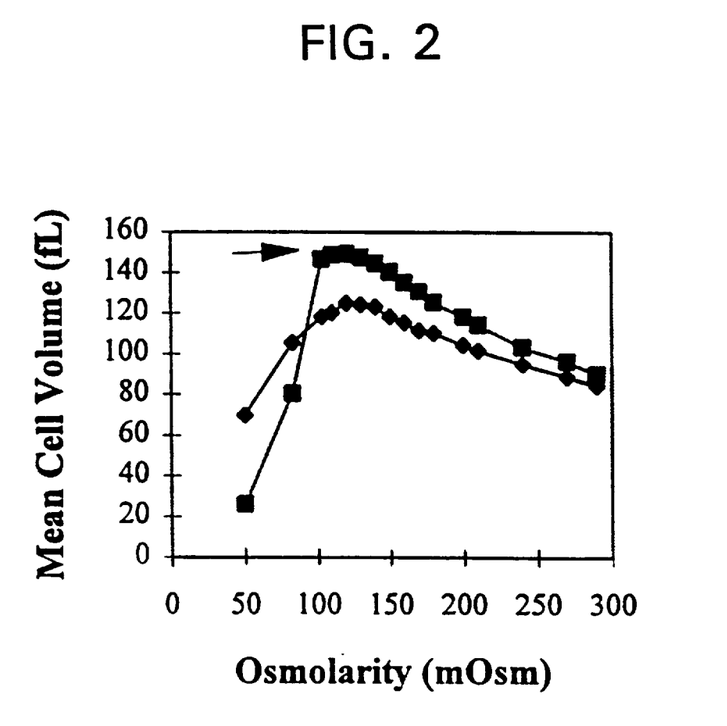
FIG. 2 demonstrates that the maximum MCV for both reticulocytes (indicated by the arrow) and mature erythrocytes can be determined by assessing mean cell volume (y axis) as a function of osmolality (x axis).

Experiments were performed to demonstrate the differential determination of the surface area of reticulocytes as distinguished from that of mature red blood cells in a blood sample. The experimental protocol was as described in Example 1. The reagent solutions described in Example 1 were prepared, and the cationic dye Oxazine 750 was added to each of the reagent solutions at a concentration of 5.5 mg/L. Aliquots of a blood sample from a patient diagnosed with sickle cell anemia and having a reticulocyte count of 12.6% were incubated in each of the fifteen reagent solutions and were analyzed as described in Example 1. As shown in FIG. 2, the maximum MCV for both reticulocytes (indicated by the arrow) and mature red blood cells was determined. Surface area calculations for the two populations are presented in Table 4. It is noted that the reticulocyte population has a 12% greater surface area than that of the gated cell population.

The method of the invention provides for the first time accurate measurements of surface area of both the reticulocyte and red cell populations in a blood sample. This, in turn, can shed new light on reticulocyte membrane remodeling in various red cell disorders. Also, since recent studies have shown that the widely-used osmotic fragility test fails to diagnose approximately 15 to 20% of cases of HS, in spite of cell surface area loss due to concomitant cell dehydration (Cynober T. et al., J. Lab. Clin. Med., 128(3): 259–269, 1996), the present invention affords more effective screening methods and reagents for this important cell disorder by its ability to directly document and determine the loss of cell surface area.

The contents of all patents, patent applications, published articles, books, references, manuals, and abstracts cited herein are hereby incorporated by reference in their entirety to more fully describe the state of the art to which the invention pertains.

As various changes can be made in the above-described subject matter without departing from the scope and spirit of

TABLE 4

| SAMPLE | MCV (fL) at 290 mOsm | MCV max (fL) | V 290 mOsm/ V max | Sphericity | Surface Area µM² |
|---|---|---|---|---|---|
| Gated Cells | 84.4 | 125.0 | 1.48 | 0.9992 | 120.75 |
| Reticulocytes | 90.1 | 149.4 | 1.66 | 0.9992 | 135.9 |

The human erythrocyte normally circulates for approximately 120 days. The youngest erythrocytes found in the peripheral circulation are identified by the RNA content as reticulocytes. These cells normally comprise about 1 to 2% the invention, it is intended that all subject matter contained in the above description or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A method for determining accurate and reliable cell surface area measurements and sphericity values of red blood cells in a blood sample obtained from an individual, comprising:

a) incubating aliquots of the blood sample in a series of reagent solutions comprising osmolalities in an osmotic range of from about 50 mOsm to about 290 mOsm (±1 to 10 mOsm), said reagent solutions comprising a nonionic, cationic, or zwitterionic surfactant to sphere red blood cells, a salt, and a buffer to maintain a near physiological pH;

b) applying the incubated sample aliquots of step a) to cytometric analyzer region of a flow cytometer;

c) determining red blood cell volume i) at isotonicity to provide measured mean cell volume and ii) in the range of osmolalities of step a) to provide maximal cell volume; wherein cell volume increases with decreasing osmolality of said reagent solutions until a maximum cell volume is reached;

d) applying geometric analysis at maximum cell volume to derive a mean surface area of the red blood cells; and e) determining a value of cell sphericity from the derived mean surface area and the measured mean cell volume of the red blood cells at isotonicity and physiological pH; wherein the cell sphericity value is proportional to a ratio of the measured red blood cell volume versus the red blood cell surface area.

2. The method according to claim 1, further comprising the step of determining a red blood cell count.

3. The method according to claim 1, wherein the reagent solutions in step a) further comprise a cationic dye.

4. The method according to claim 3, further comprising the step of determining a reticulocyte count.

5. The method according to claim 3, wherein the dye is selected from the group consisting of oxazines and thiazines.

6. The method according to claim 5, wherein the dye is Oxazine 750, Brilliant Cresyl Blue or New Methylene Blue.

7. The method according to claim 6, wherein the dye is Oxazine 750.

8. The method according to claim 1, wherein both cell volume and surface area are determined at isotonicity and further wherein cell volume and surface area are determined within a critical hemolytic volume range, said critical hemolytic volume range being a range of osmolalities in which 50% of the cells have lysed.

9. The method according to claim 8, wherein said isotonicity is approximately 290 mOsm (±1 to 10 mOsm) and said critical hemolytic volume range comprises osmolalities of approximately 100 to 260 mOsm (±1 to 10 mOsm).

10. The method according to claim 9, wherein said critical hemolytic volume range is about 120 to 160 (±1 to 10) mOsm.

11. The method according to claim 1, wherein in step a), said reagent solutions comprise at least one solution having an osmolality of about 290 mOsm (±1 to 10 mOsm), and at least three solutions having osmolalities within a critical hemolytic osmotic range, said range being sufficient for lysing 50% of the red blood cells in the blood sample.

12. The method according to claim 11, wherein said critical hemolytic osmotic range is from approximately 100 to 260 mOsm (±1 to 10 mOsm).

13. The method according to claim 12, wherein said critical hemolytic osmotic range is about 120 to 160 mOsm (±1 to 10 ) mOsm.

14. The method according to claim 1, wherein said series of reagent solutions comprises 15 reagent solutions having osmolalities of 290(±1 to 10) mOsm, 270(±1 to 10) mOsm, 240(±1 to 10) mOsm, 210(±1 to 10) mOsm, 200(±1 to 10) mOsm, 180(±1 to 10) mOsm, 170(±1 to 10) mOsm, 160(±1 to 10) mOsm, 150(±1 to 10) mOsm, 140(±1 to 10) mOsm, 130(±1 to 10) mOsm, 120(±1 to 10) mOsm, 110(±1 to 10) mOsm, 80(±1 to 10) mOsm and 50(±1 to 10) mOsm.

15. The method according to claim 1, wherein the buffer in the reagent solutions is selected from the group consisting of Tris[hydroxymethyl]aminomethane (Tris/Tris HCl), 3-[N-Morphilino]-propane acid (MOPS), n-[2-Hydroxyethyl]-piperazine N'[2 ethanesulfonic acid] (HEPES), 3-[N,N-bis(2-hydroxyethyl)-amino-]-2-hydroxypropane sulfonic acid (DIPSO), and sodium or potassium phosphate.

16. The method according to claim 1, wherein the surfactant is selected in the reagent solutions is selected from the group consisting of lauramidopropylbetaine, N-tetradecyl-N,N-dimethyl-3-ammonio-1-propanesulfonate (TDAPS), N-dodecyl-N,N-dimethyl-3-ammonio-1-propanesulfonate (DDAPS), cocoamidopropylbetaine, cocoamidosulfobetaine, and nonionic surfactants.

17. The method according to claim 16, wherein the surfactant is N-tetradecyl-N,N-dimethyl-3-ammonio-1-propanesulfonate (TDAPS).

18. The method according to claim 1, wherein the surfactant is present in the reagent solutions in an amount of from about 3.9 µg/ml to about 148 µg/ml.

19. The method according to claim 1, wherein the salt in said reagent solutions is a metal salt selected from the group consisting of sodium chloride, potassium chloride and lithium chloride.

20. The method according to claim 19, wherein the metal salt is sodium chloride.

21. The method according to claim 1, wherein the pH of said reagent solutions is about 6 to about 9.

22. The method according to claim 21, wherein the pH of said reagent solutions is about 7 to about 8.

23. The method according to claim 22, wherein the pH of said reagent solutions is 7.4 to 7.6.

24. The method according to claim 1, wherein said sample aliquots are incubated in said reagent solutions for about 15 to 90 minutes.

25. The method according to claim 24, wherein said sample aliquots are incubated in said reagent solutions for about 30 minutes.

26. The method according to claim 1, wherein said blood sample aliquots are mixed with said reagent solutions by an automated analyzer to form mixtures and said mixtures are reacted for about 20 to 60 seconds.

27. The method according to claim 26, wherein said mixtures are reacted for about 42 seconds.

28. The method according to claim 1, whereby said steps (a)–(e) are capable of determining a red blood cell disorder associated with loss of red blood cell membrane surface area; wherein said cell sphericity is a value proportional to a ratio of the red blood cell volume to the red blood cell surface area, with perfectly sphered cells having a sphericity value of approximately 1.0, and non-perfectly sphered cells having a sphericity value of less than 1.0; wherein red blood cells having loss of surface area and being spherocytic in the blood sample are identified by establishing a range of sphericity values for normal red blood cells, such that red blood cells having loss of surface area and being spherocytic in the blood sample have sphericity values above the normal range, but not exceeding a sphericity value of approximately 1.0; and further wherein the loss of red blood cell membrane surface area is indicative of a red blood cell disorder.

29. The method according to claim 28, wherein the red blood cell disorder is hemolytic anemia.

30. The method according to claim 29, wherein the hemolytic anemia is selected from the group consisting of hereditary spherocytosis, hereditary elliptocytosis, and pyropoikelocytosis.

31. The method according to claim 1, wherein a resultant loss of red blood cell surface area is capable of identifying units of blood that will have decreased in vivo survival time following transfusion as a result of storage.

32. The method according to claim 1, wherein said steps (a)–(e) determine whether excessive loss of surface area in red blood cells in transfusable blood units has occurred during approved storage periods.

33. A method for identifying mature red blood cells and reticulocytes which have a loss of surface area and are spherocytic in a blood sample obtained from an individual, comprising:
 a) incubating aliquots of said blood sample in a series of reagent solutions having osmolalities in an osmotic range of from about 50 mOsm to about 290 mOsm (±1 to 10 mOsm), said reagent solutions comprising a nonionic, cationic, or zwitterionic surfactant to sphere mature red blood cells and reticulocytes in the blood sample, a cationic dye compound to stain reticulocytes in the blood sample, a salt, and a buffer to maintain a near physiological pH;
 b) applying said incubated sample aliquots of step a) to a cytometric analyzer region of a flow cytometer;
 c) determining cell volume of the mature red blood cells and the reticulocytes in the blood sample, i) at isotonicity to provide measured mean cell volume and ii) in the range of osmolalities of step a) to provide maximal cell volume; wherein cell volume increases with decreasing osmolality of said reagent solutions until a maximum cell volume is reached;
 d) applying geometric analysis at maximum cell volume to derive a mean surface area of the mature red blood cells and the reticulocytes in the sample; and
 e) determining a measure of cell sphericity from the derived mean surface areas and the measured mean cell volumes of the mature red blood cells and the reticulocytes at isotonicity and physiological pH; wherein said cell sphericity is a value proportional to a ratio of the red blood cell volume to the red blood cell surface area, with perfectly sphered cells having a sphericity value of approximately 1.0, and non-perfectly sphered cells having a sphericity value of less than 1.0; and further wherein the mature red blood cells and the reticulocytes having loss of surface area and being spherocytic in the blood sample are identified by establishing a range of sphericity values for normal mature red blood cells and reticulocytes, such that mature red blood cells and reticulocytes having loss of surface area and being spherocytic in the blood sample have sphericity values above the normal range, but not exceeding a sphericity value of approximately 1.0.

34. The method according to claim 33, wherein the dye compound is selected from the group consisting of oxazines and thiazines.

35. The method according to claim 34, wherein the dye compound is Oxazine 750, Brilliant Cresyl Blue or New Methylene Blue.

36. The method according to claim 35, wherein the dye compound is Oxazine 750.

37. The method according to claim 33, wherein both cell volume and surface area are determined at isotonicity and further wherein cell volume and surface area are determined within hemolytic volume range, said critical hemolytic volume range being a range of osmolalities in which 50% of the red blood cells have lysed.

38. The method according to claim 37, wherein said isotonicity is approximately 290 mOsm (±1 to 10 mOsm) and said critical hemolytic volume range comprises osmolalities of approximately 100 to 260 mOsm (±1 to 10 mOsm).

39. The method according to claim 38, wherein said critical hemolytic volume range comprises osmolalities of about 120 to 160 mOsm (±1 to 10 ) mOsm.

40. The method according to claim 33, wherein in step a), said series of reagent solutions comprises at least one solution having an osmolality of about 290 mOsm, and at least three solutions having osmolalities within a critical hemolytic osmotic range of about 100 to about 260 mOsm.

41. The method according to claim 33, wherein said series of reagent solutions comprises 15 reagent solutions having osmolalities of 290(±1 to 10) mOsm, 270(±1 to 10) mOsm, 240(±1 to 10) mOsm, 210(±1 to 10) mOsm, 200(±1 to 10) mOsm, 180(±1 to 10) mOsm, 170(±1 to 10) mOsm, 160(±1 to 10) mOsm, 150(±1 to 10) mOsm, 140(±1 to 10) mOsm, 130(±1 to 10) mOsm, 120(±1 to 10) mOsm, 110(±1 to 10) mOsm, 80(±1 to 10) mOsm and 50(±1 to 10) mOsm.

42. The method according to claim 33, wherein the buffer in said reagent solutions is selected from the group consisting of Tris[hydroxymethyl]amino-methane (Tris/Tris HCl), 3-[N-Morphilino]-propane acid (MOPS), n-[2-Hydroxyethyl]-piperazine N'[2 ethanesulfonic acid] (HEPES), 3-[N,N-bis(2-hydroxyethyl)-amino]-2 hydroxypropane sulfonic acid (DIPSO), and sodium or potassium phosphate.

43. The method according to claim 33, wherein the surfactant in the reagent solutions is selected from the group consisting of lauramidopropylbetaine, N-tetradecyl-N,N-dimethyl-3-ammonio-1-propanesulfonate (TDAPS), N-dodecyl-N,N-dimethyl-3-ammonio-1-propanesulfonate (DDAPS), cocoamidopropylbetaine, cocoamidosulfobetaine, and nonionic surfactants.

44. The method according to claim 43, wherein the surfactant is N-tetradecyl-N,N-dimethyl-3-ammonio-1-propanesulfonate (TDAPS).

45. The method according to claim 33, wherein the surfactant is present in the reagent solutions in an amount of from about 3.9 µg/ml to about 148 µg/ml.

46. The method according to claim 33, wherein the salt in said reagent solutions is a metal salt selected from the group consisting of sodium chloride, potassium chloride and lithium chloride.

47. The method according to claim 46, wherein the metal salt is sodium chloride.

48. The method according to claim 33, wherein the pH of said reagent solution is about 6 to about 9.

49. The method according to claim 48, wherein the pH of said reagent solutions is about 7 to about 8.

50. The method according to claim 49, wherein the pH of said reagent solutions is 7.4 to 7.6.

51. The method according to claim 33, wherein said sample aliquots are incubated in said reagent solutions for about 15 to 90 minutes.

52. The method according to claim 51, wherein said sample aliquots are incubated in said reagent solutions for about 30 minutes.

53. The method according to claim 33, wherein said blood sample aliquots are mixed with said reagent solutions by an automated analyzer to form mixtures and said mixtures are reacted for about 20 to 60 seconds.

54. The method according to a claim 53, wherein said mixtures are reacted for about 42 seconds.

55. The method according to claim 33, wherein a resultant loss of red blood cell surface area is capable of identifying units of blood that will have decreased in vivo survival time following transfusion as a result of storage.

56. The method according to claim 33, wherein said steps (a)–(e) determine whether excessive loss of surface area in red blood cells in transfusable blood units has occurred during approved storage periods.

57. A reagent composition series for determining membrane surface area and sphericity of mature red blood cells and reticulocytes in a whole blood sample, comprising at least one reagent solution having a near physiologic osmolality of about 290(±1 to 10 mOsm) and at least three reagent solutions comprising osmolalities in the range of about 260 to 100 mOsm (±1 to 10 mOsm); wherein said reagent solutions comprise a nonionic, cationic or zwitterionic surfactant for sphering red blood cells, a cationic dye compound for staining reticulo, a salt, and a buffer to maintain a near physiological pH of said reagent solutions in said reagent composition series.

58. The reagent composition series according to claim 57, wherein the buffer in said reagent solutions is selected from the group consisting of Tris [hydroxymethyl]amino-methane (Tris/Tris HCl), 3[-N-Morphilino]-propane acid (MOPS), n-[2-Hydroxyethyl]-piperazine N'[2 ethanesulfonic acid] (HEPES), 3-[N,N-bis(2-hydroxyethyl)-amino-]-2 hydroxypropane sulfonic acid (DIPSO), and sodium or potassium phosphate.

59. The reagent composition series according to claim 57, wherein the surfactant in said reagent solutions is selected from the group consisting of lauramidopropylbetaine, N-tetradecyl-N,N-dimethyl-3-ammonio-1-propanesulfonate (TDAPS), N-dodecyl-N,N-dimethyl-3-ammonio-1-propanesulfonate (DDAPS), cocoamidopropylbetaine, cocoamidosulfobetaine and nonionic surfactants.

60. The reagent composition series according to claim 59, wherein the surfactant is N-tetradecyl-N,N-dimethyl-3-ammonio-1-propanesulfonate (TDAPS).

61. The reagent composition series according to claim 59, wherein the surfactant is present in the reagent solutions in an amount of from about 3.9 µg/ml to about 148 µg/ml.

62. The reagent composition series according to claim 57, wherein the salt in said reagent solutions is a metal salt selected from the group consisting of sodium chloride, potassium chloride and lithium chloride.

63. The reagent composition series according to claim 57, wherein the pH of said reagent solutions is about 6 to about 9.

64. The reagent composition series according to claim 63, wherein the pH of said reagent solutions is about 7 to about 8.

65. The reagent composition series according to claim 64, wherein the pH of said reagent solutions is 7.4 to 7.6.

66. The reagent composition series according to claim 57, wherein said osmolality range is about 120 to 160 mOsm (±1 to 10) mOsm.

67. A method for determining the surface area of red cells and sphericity values of mature red blood cells and reticulocytes in a blood sample, comprising:

a) reacting aliquots of said blood sample with a series of reagent solutions, said series comprising at least one reagent solution having a near physiologic osmolality and at least three reagent solutions having osmolalities within an osmotic range sufficient to determine a critical hemolytic volume of the red blood cells, said critical hemolytic volume being within a range of osmolalities in which 50% of the red blood cells in the aliquots of the blood sample have lysed, said reagent solutions further comprising a nonionic, cationic, or zwitterionic surfactant to sphere the red blood cells in the sample, a salt, a cationic dye compound to stain reticulocytes and a buffer to maintain a near physiological pH;

b) applying said aliquots of the blood samples to a cytometric analyzer region of a flow cytometer;

c) determining a cell volume of the mature red blood cells and the reticulocytes in the blood sample, i) at physiologic osmolality to provide measured mean cell volumes and ii) in the range of osmolalities sufficient to determine a critical hemolytic volume of the red blood cells of step a) to provide maximal cell volume; wherein cell volume increases with decreasing osmolality of said reagent solutions until a maximum cell volume is reached;

d) applying geometric analysis at maximum cell volume to derive a mean surface area of the mature red blood cells and reticulocytes; and e) determining a value of cell sphericity from the derived mean surface areas and the measured mean cell volumes of the mature red blood cells and the reticulocytes at isotonicity and near physiological pH; wherein said cell sphericity valves are proportional to a ratio of the red blood cell volume versus the red blood cell surface area.

68. The method according to claim 67, wherein the dye in the reagent solutions is selected from the group consisting of oxazines and thiazines.

69. The method according to claim 68, wherein the dye is Oxazine 750, Brilliant Cresyl Blue or New Methylene Blue.

70. The method according to claim 67, wherein said physiological osmolality is approximately 290 mOsm (±1 to 10 Osm) and said osmotic range sufficient to determine said critical hemolytic volume of the red blood cells is approximately 100 to 260 mOsm (±1 to 10).

71. The method according to claim 70, wherein said osmotic range is about 120 to 160 mOsm (±1 to 10) mOsm.

72. The method according to claim 67, wherein said series of reagent solutions comprises 15 reagent solutions having osmolalities in the range of 290(±1 to 10) mOsm, 270(±1 to 10) mOsm, 240(±1 to 10) mOsm, 210(±1 to 10) mOsm, 200(±1 to 10) mOsm, 180(±1 to 10) mOsm, 170(±1 to 10) mOsm, 160(±1 to 10) mOsm, 150(±1 to 10) mOsm, 140(±1 to 10) mOsm, 130(±1 to 10) mOsm, 120(±1 to 10) mOsm, 110(±1 to 10) mOsm, 80(±1 to 10) mOsm and 50(±1 to 10) mOsm.

73. The method according to claim 67, wherein the buffer in said reagent solutions is selected from the group consisting of Tris[hydroxymethyl]amino-methane (Tris/Tris HCl), 3-[N-Morphilino]-propane acid (MOPS), n-[2-Hydroxyethyl]-piperazine N'[2 ethanesulfonic acid] (HEPES), 3-[N,N-bis( 2-hydroxyethyl)-amino-]-2 hydroxypropane sulfonic acid (DIPSO), and sodium or potassium phosphate.

74. The method according to claim 67, wherein the surfactant in said reagent solutions is selected from the group consisting of lauramidopropylbetaine, N-tetradecyl-N,N-dimethyl-3-ammonio-1-propanesulfonate (TDAPS), N-dodecyl-N,N-dimethyl-3-ammonio-1-propanesulfonate (DDAPS), cocoamidopropylbetaine, cocoamidosulfobetaine and nonionic surfactants.

75. The method according to claim 67, wherein the surfactant is present in the reagent solutions in an amount of from about 3.9 µg/ml to about 148 µg/ml.

76. The method according to claim 67, wherein the salt in said reagent solutions is a metal salt selected from the group consisting of sodium chloride, potassium chloride and lithium chloride.

77. The method according to claim 67, wherein the pH of said reagent solutions is about 6 to about 9.

78. The method according to claim 77, wherein the pH of said reagent solutions is about 7 to about 8.

79. The method according to claim 67, wherein said aliquots are incubated in said reagent solutions for about 15 to 90 minutes.

80. The method according to claim 79, wherein said aliquots are incubated in said reagent solutions for about 30 minutes.

81. The method according to claim 67, wherein said blood sample aliquots are mixed with said reagent solutions by an automated analyzer to form mixtures and said mixtures are reacted for about 20 to 60 seconds.

82. The method according to claim 81, wherein said mixtures are reacted for about 42 seconds.

83. The method according to claim 67, wherein a resultant loss of red blood cell surface area is capable of identifying units of blood that will have decreased in vivo survival time following transfusion as a result of storage.

84. The method according to claim 67, wherein said steps (a)–(e) determine whether excessive loss of surface area in red blood cells in transfusable blood units has occurred during approved storage periods.

85. A method for determining a red blood cell disorder associated with loss of red blood cell membrane surface area, based on a blood sample obtained from an individual, comprising:
   a) incubating aliquots of the blood sample in a series of reagent solutions comprising osmolalities in an osmotic range of from about 50 mOsm to about 290 mOsm (±1 to 10 mOsm), said reagent solutions comprising a nonionic, cationic, or zwitterionic surfactant to sphere red blood cells, a salt, and a buffer to maintain a near physiological pH;
   b) applying the incubated sample aliquots of step a) to a cytometric analyzer region of a flow cytometer;
   c) determining red blood cell volume i) at isotonicity to provide measured mean cell volume and ii) in the range of osmolalities of step a) to provide maximal cell volume; wherein cell volume increases with decreasing osmolality of said reagent solutions until a maximum cell volume is reached;
   d) applying geometric analysis at maximum cell volume to derive a mean surface area of the red blood cells; and
   e) determining a cell sphericity value from the derived mean surface area and the measured mean cell volume at isotonicity and physiological pH; wherein said cell sphericity is a value proportional to a ratio of the red blood cell volume to the red blood cell surface area, with perfectly sphered cells having a sphericity value of approximately 1.0, and non-perfectly sphered cells having a sphericity value of less than 1.0; wherein red blood cells having loss of surface area and being spherocytic in the blood sample are identified by establishing a range of sphericity values for normal red blood cells, such that red blood cells having loss of surface area and being spherocytic in the blood sample have sphericity values above the normal range, but not exceeding a sphericity value of approximately 1.0; and further wherein the loss of red blood cell membrane surface area is indicative of a red blood cell disorder.

86. A method for determining accurate and reliable cell surface area measurements and sphericity values of reticulocytes in a blood sample obtained from an individual, comprising:
   a) incubating aliquots of the blood sample in a series of reagent solutions comprising osmolalities in an osmotic range of from about 50 mOsm to about 290 mOsm (±1 to 10 mOsm), said reagent solutions comprising a nonionic, cationic, or zwitterionic surfactant to sphere reticulocytes in the sample, a cationic dye compound to stain reticulocytes, a salt, and a buffer to maintain a near physiological pH;
   b) applying the incubated sample aliquots of step a) to a cytometric analyzer region of a flow cytometer;
   c) determining a cell volume of the reticulocytes, i) at isotonicity to provide measured mean cell volume and ii) in the range of osmolalities of step a) to provide maximal cell volume; wherein cell volume increases with decreasing osmolality of said reagent solutions until a maximum cell volume is reached;
   d) applying geometric analysis at maximum cell volume to derive a mean surface area of the reticulocytes in the sample; and
   e) determining a value of reticulocyte sphericity from the derived mean surface area and the measured mean cell volume of the reticulocytes at isotonicity and physiological pH; wherein the reticulocyte sphericity value is proportional to a ratio of the reticulocyte volume versus the reticulocyte surface area.

87. The method according to claim 86, wherein the cationic dye is selected from the group consisting of oxazines and thiazines.

88. The method according to claim 76, wherein the dye is Oxazine 750, Brilliant Cresyl Blue or New Methylene Blue.

* * * * *

UNITED STATES PATENT AND TRADEMARK OFFICE
CERTIFICATE OF CORRECTION

PATENT NO.    : 5,830,764
DATED         : NOVEMBER 3, 1998
INVENTOR(S)   : M.P. SORETTE

It is certified that errors appear in the above-identified patent and that said Letters Patent is hereby corrected as shown below:

Column 13, claim 1, line 32, delete the word "measured".

Column 16, claim 37, line 6, insert the word --a-- between the words "within" and "hemolytic".

Column 17, claim 57, line 23, delete "reticulo" and insert the word --reticulocytes--.

Signed and Sealed this

Thirtieth Day of November, 1999

Attest:

Q. TODD DICKINSON

Attesting Officer

Acting Commissioner of Patents and Trademarks